United States Patent
Fukatsu et al.

(10) Patent No.: US 8,731,263 B2
(45) Date of Patent: May 20, 2014

(54) DIAGNOSTIC IMAGING SUPPORT EQUIPMENT

(75) Inventors: Hiroshi Fukatsu, Nagoya (JP); Maki Minakuchi, Otawara (JP); Muneyasu Kazuno, Nasushiobara (JP); Kenichi Niwa, Otawara (JP); Hiroyuki Yamasaki, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 858 days.

(21) Appl. No.: 12/032,266

(22) Filed: Feb. 15, 2008

(65) Prior Publication Data

US 2008/0212854 A1  Sep. 4, 2008

(30) Foreign Application Priority Data

Feb. 16, 2007 (JP) ................... 2007-037118

(51) Int. Cl.
*G06K 9/00* (2006.01)
(52) U.S. Cl.
USPC ............................ 382/131; 382/128; 382/132
(58) Field of Classification Search
USPC ....................... 382/128–132; 705/2
See application file for complete search history.

(56) References Cited

U.S. PATENT DOCUMENTS

| | | | |
|---|---|---|---|
| 2004/0076342 A1* | 4/2004 | Wolff et al. | 382/294 |
| 2005/0281446 A1* | 12/2005 | Glukhovsky et al. | 382/128 |
| 2006/0238546 A1* | 10/2006 | Handley et al. | 345/619 |
| 2007/0065044 A1* | 3/2007 | Park et al. | 382/305 |
| 2007/0083396 A1* | 4/2007 | Kanada et al. | 705/3 |
| 2007/0160276 A1* | 7/2007 | Chen et al. | 382/128 |
| 2008/0212861 A1* | 9/2008 | Durgan et al. | 382/131 |
| 2008/0298660 A1 | 12/2008 | Yamagata | |

FOREIGN PATENT DOCUMENTS

| | | | |
|---|---|---|---|
| CN | 101336843 A | | 1/2009 |
| JP | 2001120541 A | * | 5/2001 |
| JP | 2006-262977 | | 10/2006 |
| JP | 2007-167634 | | 7/2007 |

OTHER PUBLICATIONS

U.S. Appl. No. 12/246,117, filed Oct. 6, 2008, Yamagishi, et al.
U.S. Appl. No. 12/260,395, filed Oct. 29, 2008, Futami, et al.
U.S. Appl. No. 12/100,736, filed Apr. 10, 2008, Matsue, et al.
U.S. Appl. No. 12/107,356, filed Apr. 22, 2008, Kazuno, et al.
U.S. Appl. No. 12/100,780, filed Apr. 10, 2008, Kazuno, et al.

* cited by examiner

*Primary Examiner* — Robert Kim
*Assistant Examiner* — David E Smith
(74) *Attorney, Agent, or Firm* — Oblon, Spivak, McClelland, Maier & Neustadt, L.L.P.

(57) ABSTRACT

The present invention comprises: a data storage unit for storing series image data obtained by medical image acquisition equipment and object data containing image acquisition conditions for the series image data and the specific information for specifying other series image data related to the series image data; an information management unit for generating a thumbnail image that represents combination information of the presently obtained series image data and the past related series image data by referring to the object data; and a display unit for displaying the thumbnail image.

6 Claims, 6 Drawing Sheets

(A) EXAMPLE OF PRESENT IMAGE DATA

(B) EXAMPLE OF OBJECT DATA
- SPECIFYING INFORMATION OF PRESENT IMAGE DATA
- EXAMINATION CONDITIONS
- KEY IMAGE FOR PRESENT IMAGE : 1
- IMAGING POSITION CORRECTION INFORMATION : +10 (UPPER) RELATIVE TO FIRST PAST IMAGE DATA
- SPECIFYING INFORMATION OF FIRST PAST IMAGE DATA
- KEY IMAGE FOR FIRST PAST IMAGE DATA : 3
- ……………

(C) EXAMPLE OF ONE SHEET OF IMAGE DATA

FIG. 4A

OBJECT DATA — NORMAL DATA

SELECTION OF OBJECT DATA

FIG. 4B

PRESENT IMAGE DATA — FIRST PAST IMAGE DATA 1 — SECOND PAST IMAGE DATA 2

SELECTION OF COMPARISON DATA

FIG. 4C

PRESENT IMAGE DATA — FIRST PAST IMAGE DATA 1

FIG. 5

DIAGNOSTIC IMAGING SUPPORT EQUIPMENT

BACKGROUND OF THE INVENTION

1. Field of the Invention

The present invention relates to diagnostic imaging support equipment that facilitates the observation of images obtained per a test by medical image acquisition equipment, such as X-ray CT and MRI (hereinafter referred to as "modality"), and other related images.

2. Description of the Related Art

The test images are managed according to a format specified by DICOM (Digital Imaging and Communication in Medicine). According to the DICOM-specified format, in one examination, one or more series of images are obtained. Each of these series has multiple images. On these test images, when an examiner (although the examiner is explained below, it may be a physician) interprets, makes a diagnosis, or creates a report, it is required to monitor the course of the past and the present for the imaged site. Generally in this follow-up, presently obtained series image data (refers to multiple image data by unit obtained by modality) is compared to reference images similarly based on a past series of image data. In order to compare both, the examiner specifies the past series image data for comparison and conducts a search. Thereafter, when comparing searched series image data, the examiner needs to adjust the imaging position and display simultaneously in parallel for observation.

On the other hand, as disclosed in Japanese Unexamined Patent Application Publication 2005-301453, link data (hyperlink information) is generated to retrieve the stored image data. Then, string data that represents the link data is affixed to the report, thereby making the related image data retrievable.

However, this was inefficient in that the examiner specifies and searches two series image data for comparison. In addition, even though the examiner could search two series image data for comparison and display them in parallel by synchronizing the diffraction angle and the imaging position for the first interpretation, when trying to reuse them for the next interpretation, there has been a difficulty in that the examiner needed to adjust the synchronization.

Now, the imaging position and its synchronization are explained. For example, a berth equipped with a subject by an X-ray CT device and X-ray imaging means are located at different relative positions to be imaged. At this time, the coordinate position of a certain site in the image, which is created by imaging the certain site, is referred to as a imaging position of the site. For example, $Y_0$ refers to the longitudinal imaging position of the specific past imaged site, and $Y1$ refers to the present longitudinal imaging position of the same specific site in the image obtained in the same way as in the past. Assuming that the past imaging position $Y_0$ of the specific site equals the present imaging position $Y1$, it can be said that the imaging positions are synchronized.

When the examiner compares images of specific sites in a patient that are presently obtained by a viewer with those obtained in the past for follow-up diagnosis, it is preferred to be able to easily synchronize the imaging positions for observation.

SUMMARY OF THE INVENTION

The objective of the present invention is to facilitate the obtaining of a combination of series image data for comparison from multiple series image data and to easily display the obtained two series image data in parallel while maintaining the synchronous relationship. Furthermore, it is intended to allow the retrieval of two image data in a single adjusted synchronous relationship, while maintaining the adjusted synchronous relationship.

To achieve the above purpose, an aspect of the present invention is diagnostic imaging support equipment comprising: a data storage unit configured to store series image data obtained by medical image acquisition equipment and object data containing image acquisition conditions for said series image data and the specific information for specifying other series image data related to said series image data; an information management unit configured to generate combination information of said obtained series image data and said other related series image data by referring to said object data; and a display unit configured to display said combination information.

DETAILED DESCRIPTION OF THE EMBODIMENTS

Figure 1:
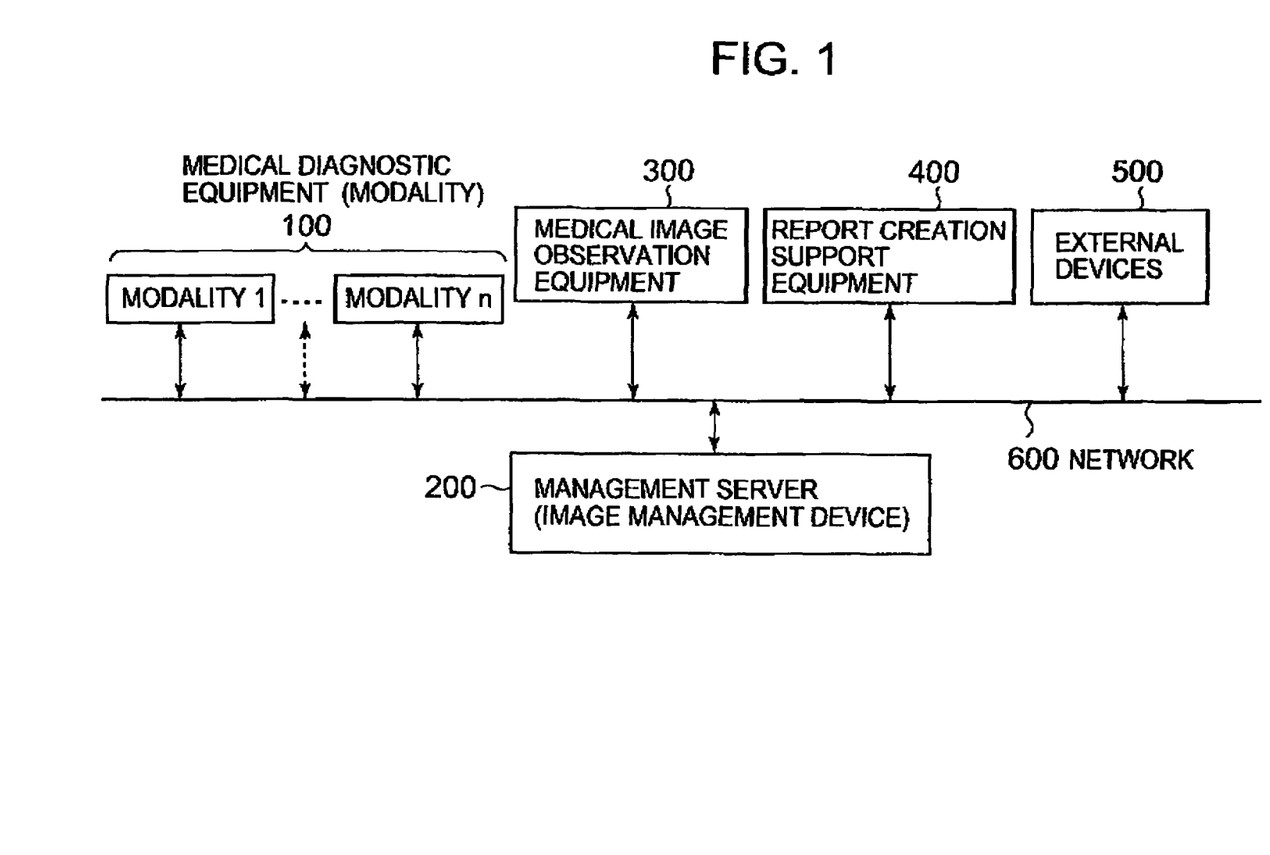
FIG. 1 is a configuration diagram of a system comprising diagnostic imaging support equipment of the present embodiment.
Figure 2:
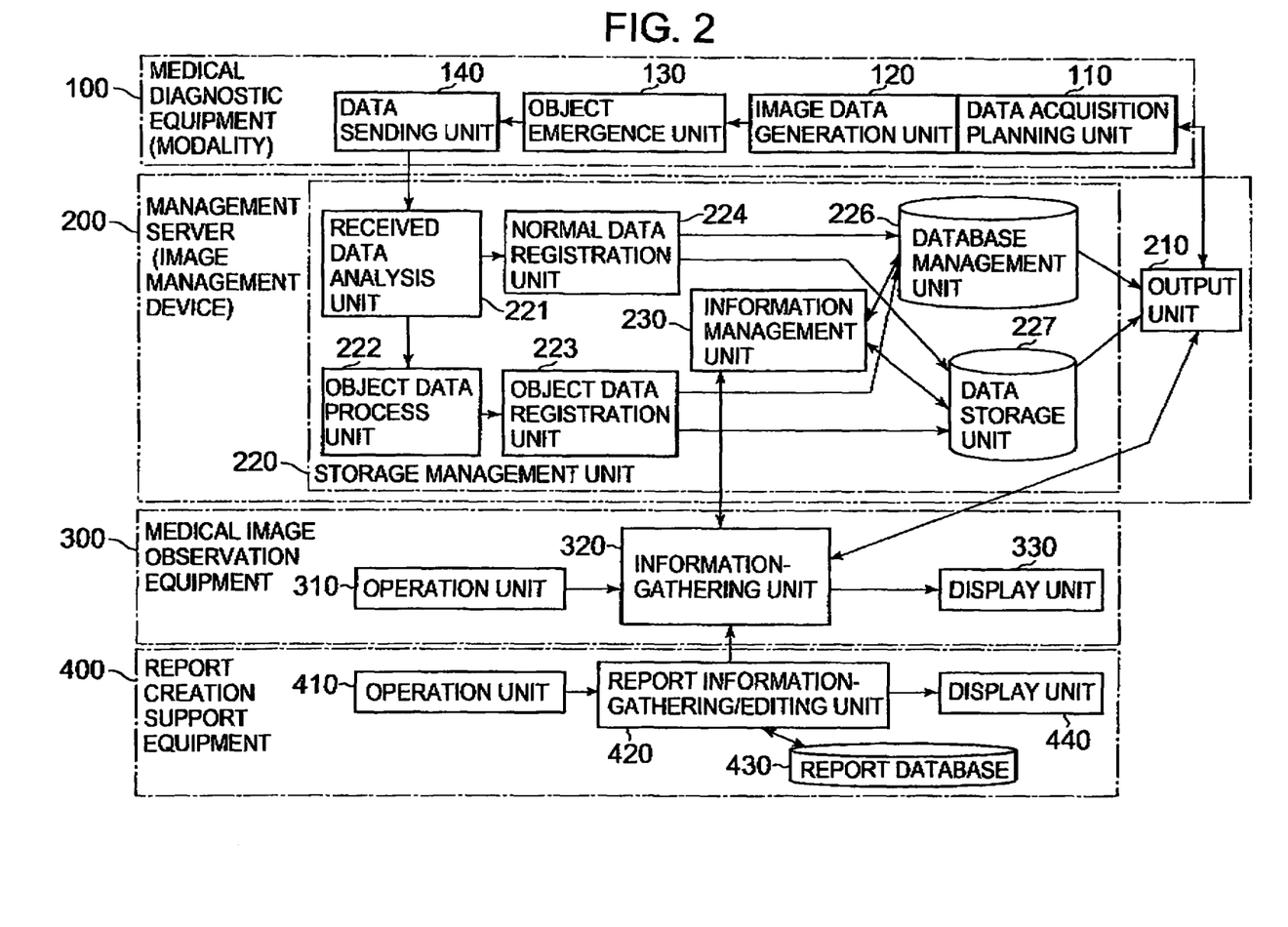
FIG. 2 is a diagram showing a functional block of diagnostic imaging support equipment pertaining to the present embodiment.
Figure 3:
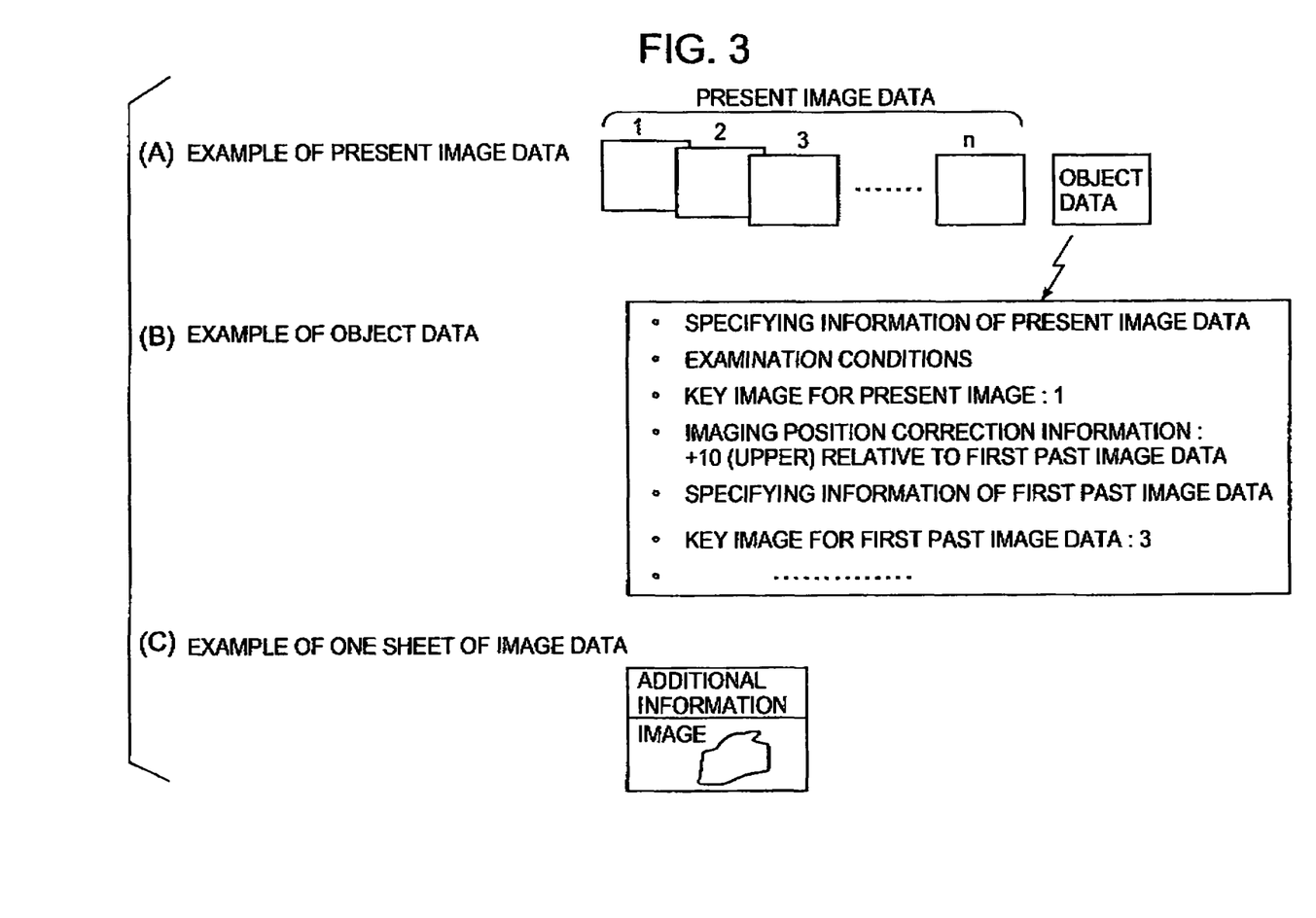
FIG. 3 is a diagram explaining image data and object data.
Figure 4A:
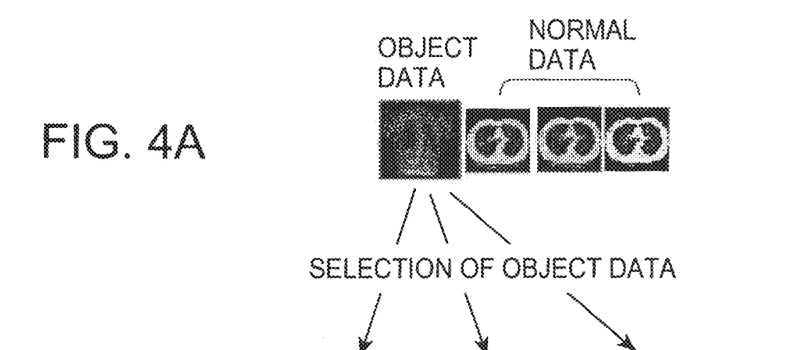
FIG. 4 is a display example when selecting desired series image data for comparison.
Figure 5:
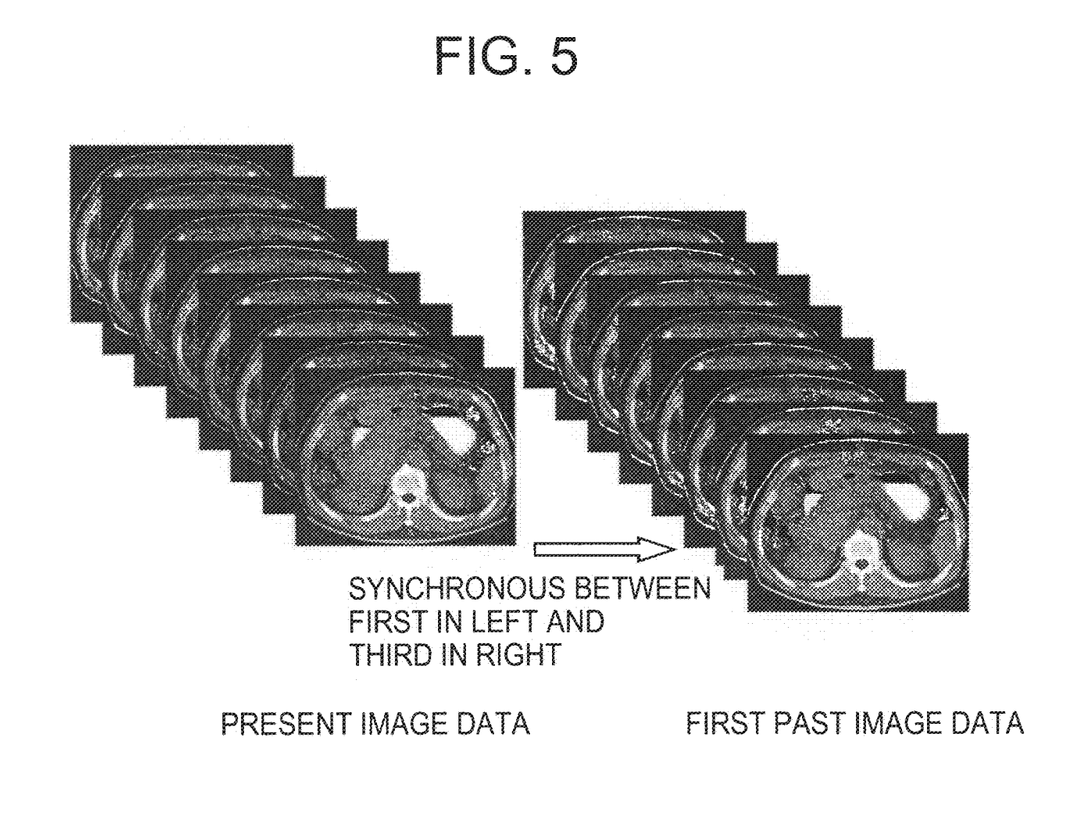
FIG. 5 is a diagram explaining the synchronous relationship between desired series image data for comparison.
Figure 6:
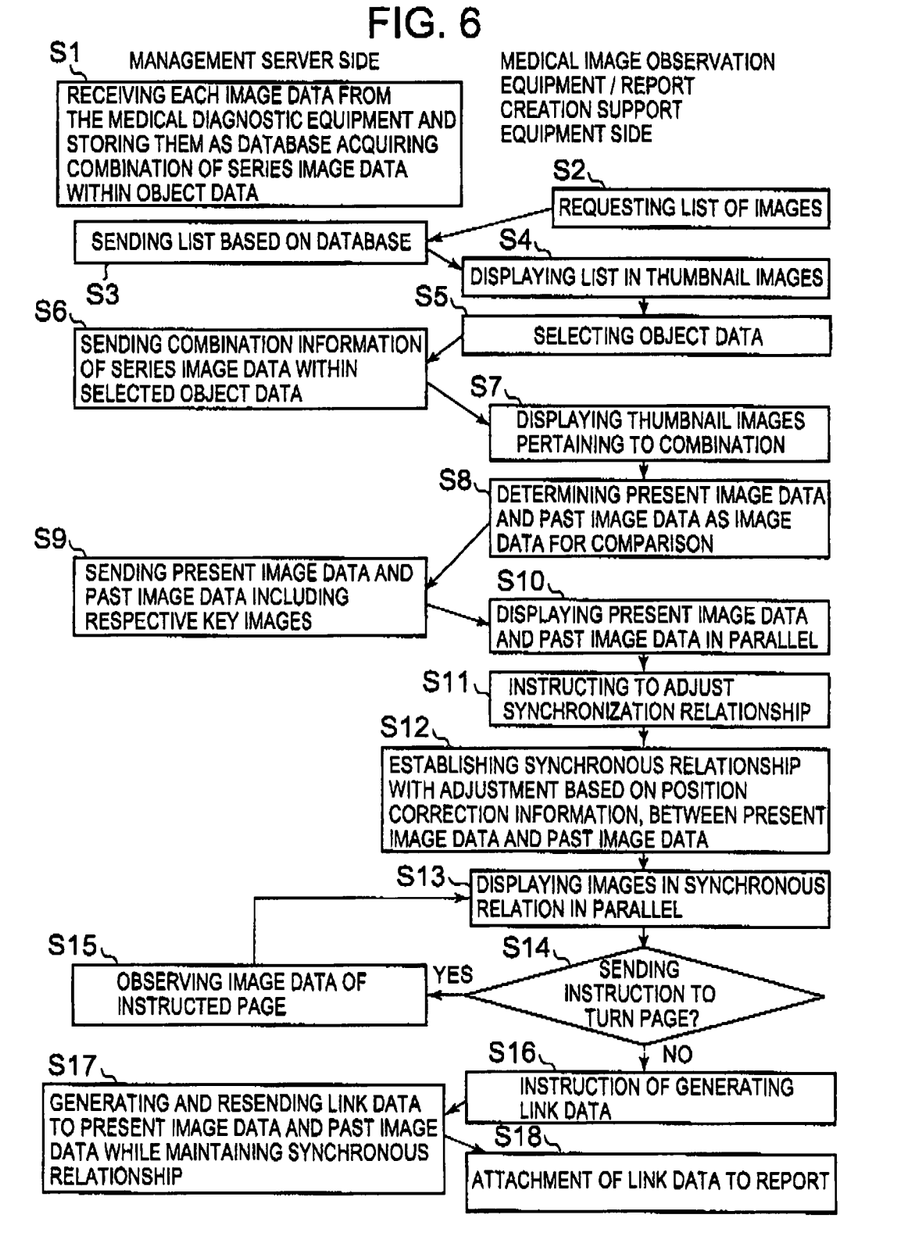
FIG. 6 is a diagram explaining a series of performances of the present embodiment.

With reference to the drawings, the embodiment of the present invention will be explained. FIG. 1 is a configuration diagram of a system comprising diagnostic imaging support equipment of the present embodiment. FIG. 2 is a diagram showing a functional block of diagnostic imaging support equipment pertaining to the present embodiment. FIG. 3 is a diagram explaining image data and object data. FIG. 4 is a display example when selecting desired series image data for comparison. FIG. 5 is a diagram explaining the synchronous relationship between desired series image data for comparison. FIG. 6 is a diagram explaining a series of performances of the present embodiment.

According to FIG. 1 and FIG. 3, the entire system is now explained. Each composition is connected by a network 600 and is mutually communicable. To medical diagnostic equipment 100 (medical image acquisition equipment), one to 'n' numbers of modalities are connected. These modalities include equipment for imaging sites in the subject, such as an X-ray CT device, MRI, and ultrasonic diagnostic equipment (hereinafter referred to as "medical diagnostic equipment 100" representatively, or "modality" when individual modality should be noted).

A management server 200, having functions of the image management unit, stores and manages image data sent from the medical diagnostic equipment 100 in addition to providing the data to medical image observation equipment 300, report creation support equipment 400, external devices 500 or the like (details will be described below). The medical image observation equipment 300 is a so-called viewer that functions as support equipment for the examiner to retrieve image data from the management server 200, interpret the image, observe, and make a diagnosis. In addition, the medical image observation equipment 300 sends instructions to the management server 200 for image management, and functions as an image management unit together with the management server 200 (details will be described below). This medical image observation equipment 300 is a computer having a capacity for sufficiently observing images based on the image data stored and managed by the management server 200 in addition to storage capacity.

The report creation support equipment 400 is a computer that incorporates software for making diagnoses or creating examination reports. It enables the description of link data (e.g. hyperlink data; it may be protection information having a protect function for protection from the outside) in the report. It allows the retrieval of specified images designated by link data from the management server 200 by opening a report with the report creation support equipment 400 or the external equipment 500 and clicking the link data described therein, and observing the images.

The medical image observation equipment 300 and the report creation support equipment 400 may be integrated or stand-alone. In addition, both may be on the management server 200 side and directly connected to the management server 200 without involving the network 600. Furthermore, although the medical diagnostic equipment 100 serves as a medical image acquisition device, it may function to retrieve the image data once taken into the management server 200 and display it on its own display unit for observation.

Composition/Performance of the Diagnostic Imaging Support Equipment

The diagnostic imaging support equipment according to the present invention refers to the management server 200 (image management unit) among elements pertaining to FIG. 1 and FIG. 2 in a limited sense. While in a broad sense, it refers to one containing a combination of the management server 200 and the medical image observation equipment 300, and further, the management server 200, the medical image observation equipment 300, and the report creation support equipment 400. Hereinafter, the details will be explained including the medical diagnostic equipment 100.

In FIG. 2, the medical diagnostic equipment 100 (medical image acquisition device) utilizes the image data generation unit 120 to output tomographic image data from data obtained by irradiating X-rays on the subject. In this case, the data acquisition planning unit 110 preliminarily retrieves the past image data pertaining to the same imaging position in the same subject (past image data) and displays them to make them referable to the examiner. Referring to this, under the substantially same imaging conditions, within the substantially same imaging range, the image data generation unit 120 is activated to obtain the present image data (present image data). The object emergence unit 130, as mentioned above, for example, manages as the object data together with the obtained present image data: specific information to specify multiple past image data if any; imaging conditions in the examination; and the examination conditions including imaging range. They are sent to the management server 200 together with the image data via the data sending unit 140.

Referring to FIG. 3 herein, the image data and object data are explained. One examination unit contains one or more series. FIG. 3(A) indicates series image data as an example, which is related to the present imaging among multiple series (hereinafter referred to as "present image data"). One series image data is associated with "n" number of image data and object data. That is, to a series of image data contained in one series, at least one object data is assigned. The object data, as shown in FIG. 3(B), includes identification data for specifying the present image data, information that represents the examination conditions, information for specifying a key image to be the key for the present image, information for specifying series image data obtained in the past and referred to at this time (hereinafter referred to as "past image data"), and information for specifying the key image of the past image data. In addition, it may include image data obtained for positioning.

Furthermore, as object data, imaging position correction information is used to display the present image data and the past image data synchronously at an anatomically similar position. In addition, as shown in FIG. 3(C), each sheet of series image data shown in FIG. 3(A) is comprised of image data, information for specifying the image data, imaging conditions, and additional information on the site. The example shown in FIG. 3(A) indicates series image data (also referred to as normal image data) that manages multiple sheets of image data obtained in one examination on a imaging basis (series unit) therein.

In FIG. 2, the storage management unit 220 of the management server 200 comprises a received data analysis unit 221, object data process unit 222, object data registration unit 223, normal data registration unit 224, database management unit 226, and data storage unit 227.

The received data analysis unit 221 analyzes image data sent from each modality in the DICOM format and classifies whether it is object data or normal image data. If it is the former, it is sent to the object data process unit 222. If it is the latter, it is sent to the normal data registration unit 224. The following explanation assumes that object data is sent.

The object data process unit 222 compresses the object data presently associated with the image data and sends it to the object data registration unit 223. The object data registration unit 223 stores the object data in the data storage unit 227 and retrievably registers it into the database management unit 226 (hereinafter, the term "registration" means storing manageably).

As such, since the data is stored or managed by the data storage unit 227 and the database management unit 226, the past object data is also contained.

The normal data registration unit 224 stores the normal image data in the data storage unit 227 and registers it into the database management unit 226.

The database management unit 226, with a database format, comprises a means to create/change (including addition, deletion, and modification) a database according to the instructions from each unit, by writing the received data, and memory to store the created database. The data storage unit 227 has memory to store the image data.

As mentioned below, when the information management unit 230 and the information-gathering unit 320 establish a synchronous imaging position for each image pertaining to a combination designated to be compared (for example, the present image data and the past image data), the database management unit 226 can set the synchronous relationship into the database. For example, it stores the fact that the first present image data is synchronized with the third past image data taken a month ago. When all series image data is retrieved from the output unit 210, it retrieves the first present image data and the third past image data simultaneously and thereafter allows output while maintaining the synchronous relationship between the second present image data and the fourth past image data. Hereinafter, the term "synchronous" may refer to the fact that the imaging positions of the present image data and the past image data are identical.

The information management unit 230 and the information-gathering unit 320, together with the database management unit 226 or/and data storage unit 227, are adapted to carry out the following performances of (1)-(5). These performances are mainly carried out when the below mentioned information-gathering unit 320 sends a request from the examiner for image observation. In the performance (5), the link data creation process is explained. Since it is only necessary to synchronize the present image data and the past image data in the present embodiment, processing the performance (5) is determined to be optional.

(1) The information management unit 230 generates information retrievable by management units stored in the data storage unit 227. As mentioned above, multiple series units of information are obtained in one examination unit; however, the description below is for each series of information. As shown in FIG. 4(A), this information includes the object data 1000 and the normal data 1001 (image data), which is assigned to each series. Accordingly, each series includes at least one object 1000. For example, the object data 1000 is generated by the information management unit 230, based on the database, such that the key image data specified by the object data 1000 is retrieved from the data storage unit 227 and displayed as a thumbnail image. One of the normal data 1001 without the object data 1000 is changed by the information management unit 230 into a thumbnail as it is. Then, the information management unit 230 outputs a list of generated thumbnail images to the information-gathering unit 320, in response to the observation request. The information-gathering unit 320 instructs the display unit 330 to perform displaying. Any of the thumbnail images may be preliminarily created and stored in the data storage unit 227 so as to be retrieved from the database management unit 226 upon an observation request.

(2) For example, when the examiner designates the object data 1000 (left end in FIG. 4(A)) of the present image data shown in FIG. 4(A) through the information-gathering unit 320, the information management unit 230, from the object data 1000 of the present image data, refers to the specific information of the key image for the past image data (the first past image data 1003, the second past image data 1004) that relates to the present image data 1002 and belongs to other series. Then, the key image for the past image data is retrieved from the data storage unit 227 to create a thumbnail image for the key image. The information management unit 230 generates a thumbnail image for the key images for each series, when multiple series are associated with the same object data (for example, the first past image data 1003, the second past image data 1004). Any of the thumbnail images may be preliminarily created and stored in the data storage unit 227 so as to be retrieved from the database management unit 226 upon an observation request.

Figure 4B:
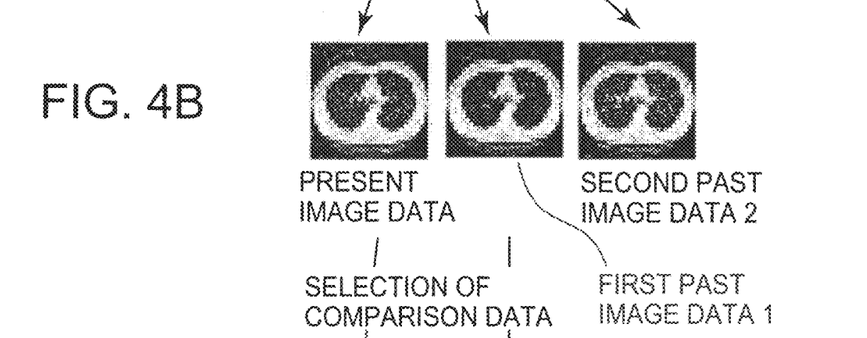

Next, as shown in FIG. 4(B), when the object data 1000 is designated, one or multiple past image data belonging to the corresponding other series is specified. FIG. 4(B) shows the first past image data 1003 and the second past image data 1004. In some cases, the number of past image data, that is corresponding series, may be one, two or more. When the number of past image data is only one, the first past image data 1003 is retrieved (since there is only one past image data, the second one 1004 is not retrieved), and a combination of the present image data 1002 and the first past image data 1003 is created. On the other hand, when there the number of past image data is multiple, a combination of the present image data 1002 and the related past image data corresponding to the selection (the first past image data 1003 in this case) is created.

In either case, the information management 230 generates a combination of thumbnail images of the key images for the present image data 1002 and the related first past image data 1003. The created combination as a list of the thumbnail images is output to the information-gathering unit 320. The information-gathering unit 320 instructs the display unit 330 to display them.

Figure 4C:
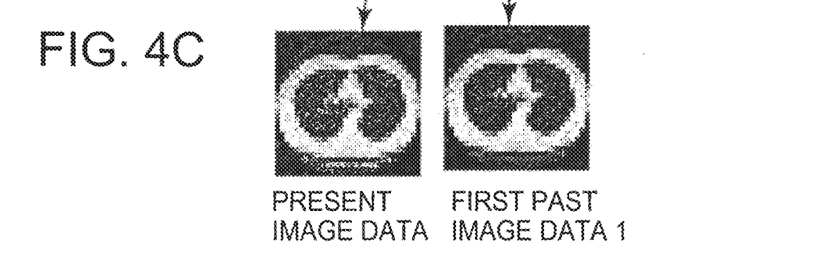

(3) In FIG. 4(B), among the thumbnail images, the present one and multiple past ones are combined to be three image data. Wherein, the information-gathering unit 320 specifies two thumbnail images pertaining to the image data for comparison from the operation unit 310, for example, two thumbnail images of the present image data 1002 and the first past image data 1003 in FIG. 4(B). Next, as shown in FIG. 4(C), the present image data 1002 and the first past image data 1003 pertaining to the specified two thumbnail images are retrieved from the data storage unit 227 via the output unit 210 and displayed on the display unit 330. In this case, they may be synchronously displayed on the basis of the key image of the present image data or the past image data, or the image that synchronizes first in both image data may be displayed synchronously.

(4) The information-gathering unit 320 refers to the object data 1000 associated with the present image data 1002 via the information management unit 230 and establishes the synchronization of the imaging position between the present image data and the past image data by referring to the position correction information or the like. It allows for the information-gathering unit 320 to ensure the synchronization of the imaging position for two image data to be compared. For example, when the information-gathering unit 320 refers to the object data 1000 indicated by FIG. 3(B), the key image of the present image data 1002 comes tenth, and the imaging position correction information indicates +10. The position correction information is the difference in a relative coordinate, which is contained in the object data and provided as data for correcting deviance in the coordinate at the anatomically similar imaging position of the present image data and the past image data. This position correction corrects deviance in the relative position of the present image data and the past image data.

In this example, as a result of synchronizing the imaging position by applying the corrected coordinate to the present examination image or the past examination image, as shown in FIG. 5, if the first present image data and the third past image data are situated at the same imaging position, it is determined as a synchronous position. Furthermore, the key image information of the present examination image comes first, and the third past examination image at the synchronous position with the key image is determined as the first display image. For example, when the key image of the present examination image is the tenth, the key image of the corresponding past examination image is the twelfth. Then, this synchronous information and image information are sent to the information-gathering unit 320 and displayed on the display unit 330. When the examiner instructs turning the page via the operation part 310, the information-gathering unit 320 causes to display the pages in the synchronous relationship in parallel (side-by-side display). For example, the first, second, ... of present image data are displayed synchronously with the third, fourth, ... of past image data.

To establish the synchronous position, it may be constructed such that the examiner refers to the object data displayed on the display unit 330, such as the medical image observation equipment 300 and sets an instruction that "synchronize the third present image data and the first past image data by moving the image position of the present image data upward by +10" by the operation unit 310, and after receiving the instruction, the information-gathering unit 320 performs as mentioned above based on the setting. It may also be constructed in such a way so that to perform the synchronous instruction, the numerals that show the number of image page, such as the present image data 1, 2, 3, 4, 5 . . . and the past image data 1, 2. 3, 4, 5 . . . , are displayed, and then, the synchronous instruction is output by dragging the present image data 1 to the reference data 3 by means of the operation unit 310. FIG. 5 shows the synchronous relationship.

In addition, it may be constituted such that the present image data established by correcting the synchronization of the position relationship is registered into the database management unit 226 via the information management unit 230 and stored into the data storage unit 227, and thereafter, both image data are easily synchronized and retrieved. Synchronization of the comparative display between series images comprising multiple slice images refers to synchronization of the slice positions. That is, since it is difficult to image a range of the completely same site of the subject in the present imaging and the previous imaging, the slice image of the first present image and the fifth image may be at the same position. In such cases, information that shows the slice deviance may be stored in the object data associated with the present image as position correction information.

(5) In the present embodiment, as mentioned above, it is possible to synchronize the positional relationship. Furthermore, as follows, the synchronous relationship may be created in report data as link data. When link data (including hyperlink) is created, as information that shows the synchronous positional relationship of the image data pertaining to the combination designated for comparison, the link data may be constructed so as to be retrieved to a column of series image data corresponding to the database. In this way, when designated in the link data, referring to the database, it is possible to output the image data, which is synchronized two-series image data.

Firstly, the user enters instructions for link data creation for creating a report from the medical image observation equipment 300 or the report creation support equipment 400 via the information-gathering unit 320. Then, the user designates destination image data and a string in the report to be linked with the image data. Said link data determines a specific image or its range (a range of a number of images).

Upon instruction to generate this link data, the link data comprising a string that reflects the storage position of specific image data is generated, returned to the origin of instruction, and incorporated into the database. As mentioned above (3), another link data is also generated to retrieve both the present image data and the past image data simultaneously. At that time, as mentioned above (4), if the synchronous relationship between both image data has been established, it generates link data that reflects the storage position where the synchronization has been established. Accordingly, combination information is reflected on a string in a report as a hyperlink. Therefore, when the user designates this string, the linked image data is displayed.

The information management unit 230 determines how to synchronize and output the image data, and thus may be constructed with the output unit 210. In addition, since the information-gathering unit 320 performs on the side to request images, a part of the functional performances of the information management unit 230 and the information-gathering unit 320 may be integrated, or either one of the units may implement all the functional operations.

The medical image observation equipment 300, as partly mentioned above, is comprised of the operation unit 310, information-gathering unit 320, and display unit 330. The medical image observation equipment 300 is comprised of a computer and software that achieves viewer functions containing the following functions. However, it has sufficient functions/performances as a viewer for retrieving the image data stored in the data storage unit 227 to observe the image. In particular, it has sufficient storage capacity and image display speed.

The abovementioned (1)-(5) are mainly explained in terms of the information management unit 230. Herein, the performance is explained as the following (a)-(c) in terms of the medical image observation equipment 300, and particularly the information-gathering unit 320. It describes (a) approximately corresponding to the abovementioned (1) and (2), (b) corresponding to (3) and (4), and (c) corresponding to (5).

(a) The information-gathering unit 320, upon request from the operation unit 310, enables the sending of a request for a partial or complete list of the image data stored in the data storage unit 227, receives the list of the thumbnail images from the information management unit 230, and displays them in parallel (side-by-side display) (See FIG. 4(A)). Among the displays, in response to the selection of the object data from the operation unit 310, information on a combination of image data within the object, for example, all of the thumbnail images pertaining to the combination are displayed in parallel on the display unit 330 (See FIG. 4(B)). As shown in FIG. 4(C), when the operation unit 310 selects two image data for comparison among the displayed combination information, for example, when information on a combination of the present image data and the past image data I is selected as images for comparison, it requests the image data based on the thumbnail image (information on the selected combination) to the output unit 210. The output unit 210 inquires the database management unit 226 and the information management unit 230 for the storage position of the image data equivalent to the designated thumbnail image, retrieves the image data from the data storage unit 227 based on the storage position, and sends it to the information-gathering unit 320. The information-gathering unit 320 instructs the display unit 330 to display in parallel based on the present image data and the past image data.

(b) The information-gathering unit 320 refers to the object data for the present image data to establish the synchronization of said selected present image data and past image data for comparison and displays them in parallel. If the positional relationship synchronous to the database has already been registered, referring to the database, the synchronized image data may be retrieved and displayed in parallel. Then, in response to the operation of the wheel in the operation unit 310, the information-gathering unit 320 counts up or down the operation amount, and thereby displays pages of both image data with a shift of one image each. When retrieving one page each from the output unit 210, it instructs the output unit 210 to retrieve the storage position for retrieving two image data with a shift of one image each. By doing so, while maintaining the synchronous relationship, both image data can be continuously displayed in parallel, that is, it allows the turning of pages.

(c) Based on the instruction from the operation unit 310 or the report creation support equipment 400, a link data generation instruction is sent to the information management unit 230 regarding a specific image or its range (the number of images) for report creation to generate link data. For example, when creating a report by the report creation support equipment 400, it may be constitutionally possible that a report format has a certain link column, desired images are dragged there by the operation unit 410 (or the operation unit 310), and thereby the information-gathering unit 320 sends the link data generation instruction to the information management unit 230 to attach a link string as link data returned from the information management unit 230 to the link column (the medical image observation equipment 300, report creation support equipment 400, or the combination thereof can be implemented).

Requiring link data generation to retrieve both the present image data and the past image data simultaneously is simultaneous. For example, it can be requested by dragging two images to the abovementioned link column. Furthermore, images in a synchronous relationship are designated by dragging them simultaneously. As such, it allows images in a synchronous relationship to be retrieved simultaneously.

In FIG. 2, the report creation support equipment 400 is comprised of the operation unit 410, report information-gathering/editing unit 420, report database 430, and display unit 440. The report creation support equipment 400 is mainly comprised of a computer and software to implement functions of information-gathering and editing. It is comprised of a general computer, as the abovementioned viewer, having scarce resources compared to the medical image observation equipment 300.

In FIG. 2, the report database 430 stores the report format (equivalent to a paper) and the past created report such that they can be retrieved in the database. Based on the instruction from the operation unit, the report information gathering-editing unit 420 reads out the report paper or the past report from the report database 430, instructs the display unit 440 to display it, and completes a report based on an editing instruction from the operation unit 410, such as report creation. At that time, regarding the image data or the like, in cooperation with the information-gathering unit 320, it is also possible to display the requested image data on the display unit 440 or the display unit 330 for observation (The display unit 330 is utilized due to scarce resources of the report creation support equipment 400. Therefore, when there are sufficient resources, it may be constituted so as to function as the medical image observation equipment 300.). As mentioned above, the report creation support equipment 400 can send a link data creation instruction using a drag as a trigger, for example, by dragging desired images on the display unit 440 to the link column.

Next, a series of performances of the present embodiment is explained with reference to FIG. 6. The descriptions are partly the same as those mentioned above. FIG. 6 indicates the procedures for registering the image data in the storage management unit 220, selecting a combination of image data for comparison that is required for diagnosis or report creation, and synchronizing it.

Step S1: the database management unit 226 and/or the object data registration unit 223 create a database so as to be retrieved from the storage position of series image data sent from the medical diagnostic equipment 100 side and stores them to be retrievable. The information management unit 230 then creates the thumbnail image so that it can be read through. If there is a combination of the present image data and the past image data within the object data, it manages their key images as a pair of thumbnail images (the thumbnail images may be stored in the database as data, or created upon request for review).

Step S2, 3, 4: the examiner requests a list of images for the management server 200 by means of the medical image observation equipment 300, and based on the database, the management server 200 sends the list of thumbnail images to the medical image observation equipment 300. The medical image observation equipment 300 receives the request and displays the list in parallel.

Step S5, 6, 7: the examiner selects, for example, the thumbnail image of the present image data from displayed by the medical image observation equipment 300. The information-gathering unit 320 receives the thumbnail images pertaining to a combination of image data, which is managed as a pair within the object, from the information management unit 230 and displays them in parallel. For example, the respective key images of the present image data and the past image data are displayed.

Step S8, 9, 10: the medical image observation equipment 300 may directly determine the present image data and the past image data as image data for comparison, if there is one for each. However, if there are a number of them, it is selected based on the examiner's instruction. The respective key images of the determined or selected present image data and past image data are displayed in parallel.

Step S11, 12, 13: the examiner instructs to adjust synchronization of two image data by the medical image observation equipment 300. The information-gathering unit 320 retrieves the object data from the database and the data storage unit 227 via the information management unit 230 for reference, searches each key image to retrieve, and establishes the synchronous relationship with adjustment based on the position correction information. The information-gathering unit 320 displays in parallel, for example, the first present image data and the third past image data established synchronously with it.

Step S14, 15, 16: to view the image data in a synchronous relationship other than the first present image data and the third past image data, the examiner sends an instruction to turn the page by the operation unit 310. Depending on the instruction, the information-gathering unit 320 displays both the present image data and the past image data with a shift of the same number of pages. That is, while maintaining the synchronous relationship, it can be observed as if turning the page.

Step S 16, 17, 18: the medical image observation equipment 300 designates two image data in a synchronous relationship displayed as above to instruct the creation of link data, and thereby receives the link data of the present image data and the reference image data created and sent by the information management unit 230 to create a report with the attachment. By clicking the link data of the report, synchronous two-image data can be displayed. By turning pages, images on each page can be displayed while maintaining the synchronous relationship.

With the above mentioned construction of the present invention, a combination of information is created on the series image data obtained from this examination by utilizing at least the information contained in the object data and the other related series image data. The other related series image data includes, for example, the past series image data that is referred to in this examination. For example, since the combination of information is displayed as a thumbnail image, by selecting and deploying the displayed thumbnail image, the present series image data and other series image data, for example, the past image data can be retrieved, and images based on their image data can be displayed in parallel. Accordingly, it makes usage in interpretation easy and convenient. Furthermore, by synchronizing the imaging positions and displaying them in parallel, the present image and the past image at the same synchronous position can be observed in parallel as if turning pages, which is convenient, The abovementioned embodiment and variations do not limit the scope of the present invention. Consequently, those skilled in the art will be able to employ embodiments having each or all elements replaced with equivalents. These embodiments are also encompassed in the scope of the present invention.

What is claimed is:

1. A diagnostic imaging support equipment comprising:
a data storage unit configured to store object data and series image data of plural images obtained at different timings obtained by medical image acquisition equipment, and the object data including (1) specific information for specifying image acquisition conditions at the imaging timings, (2) information of a key image for generating a thumbnail of the present image data, (3) information of a key image for generating a thumbnail of the past image data, and (4) synchronization information to synchronize an imaging position in the present image data and the past image data;
an information management unit configured to generate a combination of plural thumbnail images based on image data of a portion of each series image data as combination information of said present image data and said past image data by referring to said object data, for displaying with a synchronization of the imaging positions between the present image data and the past image data; and
a display unit configured to display the thumbnails of the present image data and the past image data, the display unit referring to the synchronization information of the object data.

2. A diagnostic imaging support equipment according to claim 1, further comprising:
an operation unit configured to generate an instruction for retrieval of a combination of at least the present image data and the past image data from combination information displayed in said display unit; and
an information-gathering unit configured to retrieve from said storing unit at least the present image data and the past image data specified based on said instruction to display them in said display unit as an image.

3. A diagnostic imaging support equipment according to claim 2, wherein said object data further includes position correction information to adjust the imaging position between the present image data and the past image data; and
said information-gathering unit is configured to instruct said display unit to display in parallel images obtained at the same position between said present image data and said past image data, based on the object data retrieved from said storing unit.

4. A diagnostic imaging support equipment according to claim 3, wherein said information-gathering unit is configured to switch and display images by synchronizing the imaging positions between the present image data and the past image data being displayed.

5. A diagnostic imaging support equipment according to claim 3, further comprising:
a link data generation unit configured to generate link data that reflects the storing position for said at least present image data and past image data displayed in parallel, to retrieve said present image data and past image data based on said object data with said link data.

6. A diagnostic imaging support equipment according to claim 3, wherein said information management unit is configured to add an imaging position where said present image data and past image data for comparison are synchronized into said object data as information of the synchronous position; and redisplaying is based on said information of the synchronous position added into the object data.

* * * * *